United States Patent [19]

Olefsky

[11] Patent Number: 5,726,027
[45] Date of Patent: Mar. 10, 1998

[54] METHOD FOR TREATMENT OF INSULIN RESISTANCE

[75] Inventor: Jerrold M. Olefsky, Solana Beach, Calif.

[73] Assignee: The Regents of the University of California, Oakland, Calif.

[21] Appl. No.: 612,588

[22] Filed: Mar. 8, 1996

[51] Int. Cl.$^6$ .................. G01N 33/50; G01N 33/68
[52] U.S. Cl. .................. 435/7.21; 435/7.8; 436/501
[58] Field of Search .................. 435/7.21, 7.8, 435/17; 436/501

[56] References Cited

PUBLICATIONS

Liotta, AS et al. J. Biol. Chem. 269(37):22996–23001. Sep. 16, 1994.

Burke, TR et al. Biochem. Biophys. Res. Comm. 204(1):129–134. Oct. 14, 1994.

Kole, HK et al. Biochem. Biophys. Res. Comm. 209(3):817–822 Apr. 26, 1995.

Burke, TR et al. J. Med. Chem. 39(5): 1021–1027. Mar. 1, 1996.

Primary Examiner—Christina Y. Chan
Assistant Examiner—F. Pierre VanderVegt
Attorney, Agent, or Firm—Fish & Richardson, P.C.

[57] ABSTRACT

A screening method for identifying compositions which affect the binding of protein tyrosine phosphatase 1B (PTP1B) to phosphorylated insulin receptor is provided. This method measures a composition's ability to inhibit binding of PTP1B to the β-subunit of the insulin receptor rather than phosphatase activity in general. Also provided are specific phosphopeptides which affect the binding of protein tyrosine phosphatase 1B (PTP1B) to phosphorylated insulin receptor.

1 Claim, 7 Drawing Sheets

METHOD FOR TREATMENT OF INSULIN RESISTANCE

BACKGROUND OF THE INVENTION

1. Field of the Invention

This invention relates generally to insulin resistance and specifically to a method for identifying compositions which inhibit binding of protein tyrosine phosphatase 1B (PTP1B) to the β-subunit of the activated insulin receptor.

2. Description of Related Art

Diabetes mellitus is one of the most common, chronic diseases in the United States. As such, it is responsible for a great deal of morbidity and mortality. Approximately 95% of all diabetic patients in the United States have non-insulin dependent, Type II diabetes mellitus (NIDDM), and, therefore, this is the form of diabetes which accounts for the great majority of medical problems. Insulin resistance is an underlying characteristic feature of NIDDM and this metabolic defect leads to the diabetic syndrome.

There is a need to identify proteins directly related to obesity and diabetes. Such proteins are useful as markers for the early detection of susceptible individuals so that intervention regimes may be instituted for delay or prevention of obesity/diabetes disorders. A delay in the onset of diabetes would markedly reduce morbidity and mortality due to chronic complications. Further, identification of specific proteins involved in the insulin signaling cascade would allow for the design of more effective medications having specific intracellular targets.

SUMMARY OF THE INVENTION

The association of protein tyrosine phosphatase 1B (PTP1B) with the activated insulin receptor at multiple different phosphotyrosine sites implicates PTP1B as a key target in insulin receptor signal transduction. Based on this discovery, the invention provides a method of treating insulin resistance-associated disorders in a patient.

In a first aspect, the invention provides a phosphopeptide having an insulin receptor tyrosine phosphorylation site selected from the group consisting of a triple tyrosine kinase domain, a NPXY domain and tyrosine 1322 in the C-terminus of the insulin receptor.

The peptides of the invention can be used to treat a patient having an insulin resistance disorder by inhibiting a tyrosine phosphatase associated with insulin resistance. Preferably the composition is a polypeptide characterized as having an active phosphotyrosine binding site, binding to an activated insulin receptor, and having the amino acid sequence of protein tyrosine phosphatase 1B (PTP1B) with an amino acid substitution at residue 215. Substitution at this position renders PTP1B catalytically inactive.

In yet another aspect, the invention provides a screening method for identifying a composition that affects PTP1B binding to the insulin receptor, involving incubating the composition with PTP1B polypeptide or with a recombinant cell expressing PTP1B, and with a phosphorylated insulin receptor, for a time and under conditions sufficient to allow the components to interact; and determining the effect of the composition on PTP1B binding.

BRIEF DESCRIPTION OF THE DRAWINGS

FIG. 6A shows partially purified receptors from HIRc B cells or from ACT cells. FIG. 6B shows cell lysates from HIR or HIANPEY cells. FIG. 6C shows HIRc B or AK1018 cells activated in the presence of ATP.

DETAILED DESCRIPTION

Figure 1A:
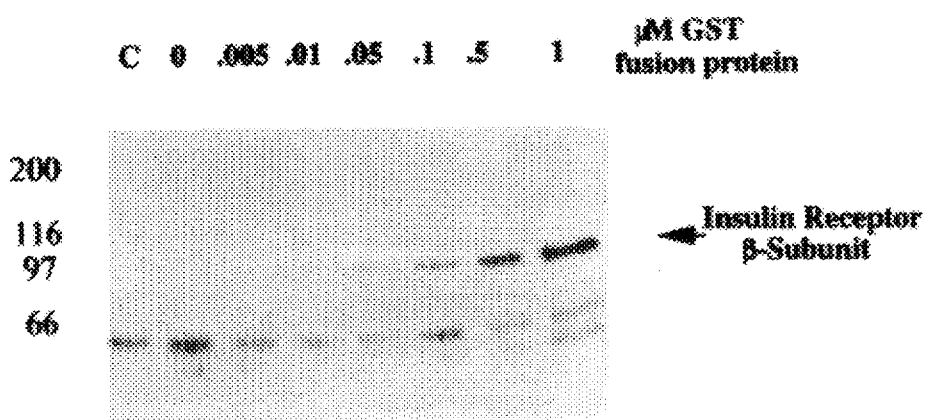
FIGS. 1A, B and C are immunoblots showing PTP1B$^{C215S}$-GST association with purified insulin receptor.

The present invention is based on the discovery that protein tyrosine phosphatase 1B (PTP1B) associates directly with the activated insulin receptor at multiple different phosphotyrosine sites. In addition, the inventors have discovered that PTP1B is tyrosine phosphorylated upon ligand stimulation. The association between PTP1B and the insulin receptor implicates PTP1B as a key player in insulin receptor signal transduction. Based on this discovery, the invention provides a method of treating insulin resistance in a patient.

Identification of PTP1B as a component of insulin receptor signal transduction also provides a target for development of inhibitors or competitive inhibitors of PTP1B binding to the insulin receptor. Specifically, PTP1B binds to the activated insulin receptor β-subunit. The present invention identifies PTP1B binding with at least three different motifs found in the insulin receptor β-subunit. These include the triple tyrosine kinase domain, the NPXY domain, and tyrosine 1322 in the receptor's C-terminus.

Therefore, in a first embodiment, the invention provides a phosphopeptide having an insulin receptor tyrosine phosphorylation site selected from the group consisting of a triple tyrosine kinase domain, a NPXY domain and tyrosine 1322 in the C-terminus of the insulin receptor. Examples of such phosphopeptides include a peptide selected from the group consisting of pYpYpY (SEQ ID NO:1); DIpYETDpYpYRK (SEQ ID NO:2); NPXpY (SEQ ID NO:3); RPXpY (SEQ ID NO:4); ASVNP-EpYFSA (SEQ ID NO:5); ASVRPEpYFSA (SEQ ID NO:6); and HIPpYTH-MNGG (SEQ ID NO:7). "pY" refers to a phospho-amino acid, for example, phosphotyrosine. The phosphopeptides include larger peptides having up to about 20 amino acids at either or both of the termini of the peptide, preferably having no more than 6–8 additional amino acids from those shown in SEQ ID NO:1–7. While not wanting to be bound by a theory, it is believed that a peptide having more than 20 amino acids will have an altered conformation as compared to the smaller linear peptides as exemplified herein.

Minor modifications of the primary amino acid sequence of the peptides of the invention described herein may result in peptides which have substantially equivalent activity to the specific peptides described herein. Such modifications may be deliberate, as by site-directed mutagenesis, or may be spontaneous. All of the peptides produced by these modifications are included herein as long as the biological activity of the peptides still exists. For example, the peptide still acts as a competitive inhibitor for the natural PTP1B insulin receptor binding site. Further, deletion of one or more amino acids can also result in a modification of the structure of the resultant molecule without significantly altering its activity. This can lead to the development of an active molecule which would have broader utility. For example, one can remove amino or carboxy terminal amino acids which may not be required for biological activity.

The peptides of the invention also include conservative variations of the peptide sequence. The invention embraces conservative variations in the remaining amino acid sequence of the peptides of the invention. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrenedivinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The invention also provides polynucleotides which encode the peptides of the invention and the modifications described. As used herein, "polynucleotide" refers to a polymer of deoxyribonucleotides or ribonucleotides, in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences.

The peptides of the invention can be used to produce antibodies which are immunoreactive or bind to epitopes of the insulin receptor. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor. As used herein, the term "selectively binds" refers to binding of an antibody (or binding fragment thereof) to an epitopic determinant to which the paratope of the antibody specifically binds. Such binding can be competitively inhibited with other antibodies produced from the same epitope of the antigen. These antibody fragments are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making antibody fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the peptides of the invention can be prepared using as an immunogen an intact polypeptide or fragments containing small peptides of interest. The polypeptide or a peptide used to immunize an animal can be derived from translated cDNA or chemical synthesis, and can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Such anti-idiotype antibodies are useful as competitive inhibitors of PTP1B binding to the insulin receptor.

The peptides of the invention can be used to treat a patient having an insulin resistance disorder. Preferably, the tyrosine phosphatase is PTP1B or a homologue thereof. As used herein, the term "insulin resistance disorder" refers to a disorder wherein insulin's effects are decreased, as evidenced by a decrease in transduction of insulin-stimulated intracellular signals. In the method of the invention, the composition preferably inhibits PTP1B binding to the β subunit of the insulin receptor, or alternatively, inhibits PTP1B phosphatase activity. Such disorders include but are not limited to non-insulin dependent diabetes mellitus (NIDDM), obesity, and polycystic ovarian syndrome.

Such compositions include an antibody which binds to PTP1B and inhibits PTP1B binding to the insulin receptor. Preferably, the antibody is a monoclonal antibody. Alternatively, it may be desirable to introduce a PTP1B antisense polynucleotide to inhibit PTP1B expression.

Antisense nucleic acids include DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target PTP1B-producing cell. The use of antisense methods to inhibit the in vitro translation of genes is well known in the art (Marcus-Sakura, *Anal.Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hamerhead-type ribozymes are preferable to tetrahymena-type ribozymes for inactivating a specific mRNA species and 18-based recognition sequences are preferable to shorter recognition sequences.

An alternative composition useful for inhibition of PTP1B activity is a PTP1B polypeptide capable of binding to the insulin receptor and having an active phosphotyrosine binding site, but lacking catalytic activity. Such a polypeptide preferably has the amino acid sequence of native PTP1B polypeptide with an amino acid substitution at residue 215. In native PTP1B, amino acid residue 215 is cysteine; substitution of this residue with a neutral amino acid, preferably serine, renders the polypeptide catalytically inactive. Such a polypeptide is useful in the method of the invention for the treatment of insulin resistance in a patient.

Phosphopeptides having an insulin receptor tyrosine phosphorylation site are also useful in the method of the invention. Examples of such phosphopeptides include the peptides of the invention, i.e., pYpYpY (SEQ ID NO:1); DIpYETDpYpYRK (SEQ ID NO:2); NPXpY (SEQ ID NO:3); RPXpY (SEQ ID NO:4); ASVNPEpYFSA (SEQ ID NO:5); ASVRPEpYFSA (SEQ ID NO:6); and HIPpYTH-MNGG (SEQ ID NO:7) as described above. Such peptides are useful for blocking PTP1B binding to the insulin receptor.

The antibodies that bind to the phosphopeptides of the invention can block or mask the PTP1B binding site on the β-subunit of the insulin receptor thus preventing signal transduction.

In yet another embodiment, the invention provides a screening method for identifying compounds or compositions which affect the binding of PTP1B to the β-subunit of the insulin receptor, or alternatively, which affect the activity of the protein (e.g., the phosphatase activity). It is preferable to affect binding rather than phosphatase activity since phosphatase activity in general is essential to the cell. Therefore, the preferred method involves incubating the compound with PTP1B polypeptide or with a recombinant cell expressing PTP1B, and with a phosphorylated insulin receptor, for a time and under conditions sufficient to allow the components to interact; and determining the effect of the composition on PTP1B binding.

The observed effect on PTP1B may be either inhibitory or stimulatory. For example, the increase or decrease of PTP1B binding can be measured by adding a labeled compound to the mixture of components, such as $^{32}$P-ATP, and observing radioactive incorporation at tyrosine to determine whether the composition inhibits binding of PTP1B. For example, if binding is blocked, PTP1B will not be phosphorylated. An increase or decrease of PTP1B binding can also be determined by standard receptor/ligand binding methods known to those of skill in the art such as Scatchard plot analysis.

Various labels may be used to determine the effect of a composition on PTP1B binding. For example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation.

The antibodies and peptides of the invention can be administered parenterally by injection or by gradual infusion over time, or intravenously, intraperitoneally, intramuscularly, subcutaneously, intracavity, or transdermally.

Other methods for delivery of the peptides include orally, by encapsulation in microspheres or proteinoids, by aerosol delivery to the lungs, or transdermally by iontophoresis or transdermal electroporation.

Preparations for parenteral administration of a peptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The following examples are intended to illustrate but not limit the invention. While they are typical of those that might be used, other procedures known to those skilled in the art may alternatively be used.

EXAMPLE 1

Materials and Methods

1. Cell Lines and Materials

Construction of an expression plasmid containing the intact or mutant human insulin receptor cDNA and the stably-transfected rat fibroblast clonal cell line HIRc B, expressing $1.25 \times 10^6$ receptors per cell and the ΔCT cell line with a 43-amino acid deletion from the C-terminus have been previously described (Kenner, et al., *Diabetes*, 44 (Suppl 1):104A, 1995; Maegawa, et al., *J. Biol. Chem.* 270:7724–7730, 1995). Cells were maintained in hypoxanthine- and guanine-deficient Dulbecco's modified Eagle's medium/F12 from Gibco BRL (Grand Island, N.Y.) supplemented with 10% fetal calf serum (Gemini Bioproducts, Calabasas, Calif.), 0.5% gentamicin 1% gluta-max (Gibco BRL) and 500 nM methotrexate (Calbiochem, La Jolla, Calif.). Chinese hamster ovary (CHO) cells were stably transfected with cDNA for the human insulin receptor (HIR) or a mutant human insulin receptor in which the NPEY domain was deleted (HIΔNPEY) (SEQ ID NO:7) (Riedel, et al., *Science* 236:197–200, 1987). Transfected CHO cells were maintained in Ham's/F12 supplemented with 10% fetal calf serum, 0.5% gentamicin, 1% gluta-max, and 400 μg/μl G418. Insulin was generously provided by Eli Lilly (Indianapolis, Ind.). Electrophoresis equipment and reagents were from Bio-Rad (Hercules, Calif.). The antiphosphotyrosine antibody and the monoclonal anti-PTP1B antibody were from Transduction Laboratories (Lexington, Ky.). The anti-insulin receptor antibody used for immunoprecipitation (1844) was generously provided by Dr. Kenneth Siddle (Cambridge, England). The anti-insulin receptor antibody used for immunoblotting was raised against a peptide (GGKKNGRILTLPRSNPS) (SEQ ID NO:8) containing the sequence of the carboxy-terminus of the human insulin receptor from 1327–1343. The goat anti-mouse igG-horseradish peroxidase antibody and the enhanced chemiluminescence (ECL) detection reagents were from Amersham Corp. (Arlington Heights, Ill.). Recombinant IRS-1 was from Upstate Biotechnology Inc. (Lake Placid, N.Y.). Nitrocellulose was from Schleicher and Schuell (Keane, N.H.). Glutathione sepharose 4B was from Pharmacia LKB Biotechnology Inc. (Alameda, Calif.). Phosphopeptides were from Quality Controlled Biochemicals (Hopkinton, Mass.) and were modeled after the amino acid sequences of specific insulin receptor tyrosine phosphorylation sites. These include the triple tyrosine kinase domain (pYpYpY), the NPXY domain (NPXpY and RPXpY), and the C-terminal tyrosine, pY1322. The sequences are: pYpYpY (SEQ ID NO:1), DipYETDpY-pYRK (SEQ ID NO:2); NPXpY (SEQ ID NO:3), A-SVNPEpYFSA (SEQ ID NO:4); and RPXpY (SEQ ID NO:5), ASVR-PEpYFSA (SEQ ID NO:6). The peptide NPXpY (SEQ ID NO:3) was not used because repeat HPLC analysis of this peptide produced two peaks indicating conformational changes in the peptide which prevented consistent phosphotyrosine binding. pY1322, HIPpYTHM-NGG (SEQ ID NO:9), was provided by Steve E. Shoelson (Joslin Diabetes Center, Harvard Medical School). All other reagents were from Sigma (St. Louis, Mo.).

2. Protein Expression and Purification

Cloning of the PTP1B$^{C215S}$-GST and the p85-GST have been described (Guan and Dixon, *J. Biol. Chem.* 266:17026–17030, 1991). The catalytically-inactive PTP1B$^{C215S}$ fusion protein consists of a portion of the catalytic domain of PTP1B from rat brain with a point mutation replacing the cysteine at position 215 with a serine residue (PTP1B$^{215S}$). The active PTP1B fusion protein is identical except that it has a cysteine in position 215. The p85-GST contains p85 residues 321 to 440, including the amino-terminal SH2 domain. p85 is the 85 kDa regulatory subunit of phosphatidylinositol-3-kinase. Expression and purification of the fusion proteins has been previously described (McClain, et al., *J. Biol. Chem.* 263:8904–8911, 1988; Berhanu, et al., *Molecular Endocrinology*, 5:1827–1835, 1991).

3. Receptor Association Assays

Insulin receptors were purified from HIRc B cells by wheat-germ agglutinin affinity chromatography and $^{125}$I-insulin binding studies were performed as previously described (Smith and Johnson, *Gene*, 67:31–40, 1988). Approximately 500 fmol of partially purified insulin receptors were used for receptor association assays as previously described (McClain, et al., supra). Where indicated, whole cell lysates were used instead of purified receptors. After overnight starvation, whole cell monolayers were stimulated with ligand for one minute at 37° C. The media was removed and 400 μl of lysis buffer was added. 100 μl of the cell lysate were then incubated with the fusion protein of interest and glutathione sepharose as previously described.

4. PTP1B Precipitation by an Anti-insulin Receptor Antibody

Monolayers of HIRc B cells at 50% confluence were starved in serum-free media for 16 hours, then stimulated with insulin, 100 ng/ml, at 37° C. for varying time intervals. The media were removed and the cells were collected in 200 μl of lysis buffer. Lysates were incubated with a monoclonal anti-insulin receptor antibody (1:100) for 4 hours and precipitates were collected with Protein A sepharose. The proteins were fractioned by non-reducing 5–15% gradient gel electrophoresis and were transferred to nitrocellulose. The blots were developed with the ECL system using either an antiphosphotyrosine antibody or an antibody specific for PTP1B.

EXAMPLE 2

Interaction Between PTP1B and the Insulin Receptor

Figure 1B:
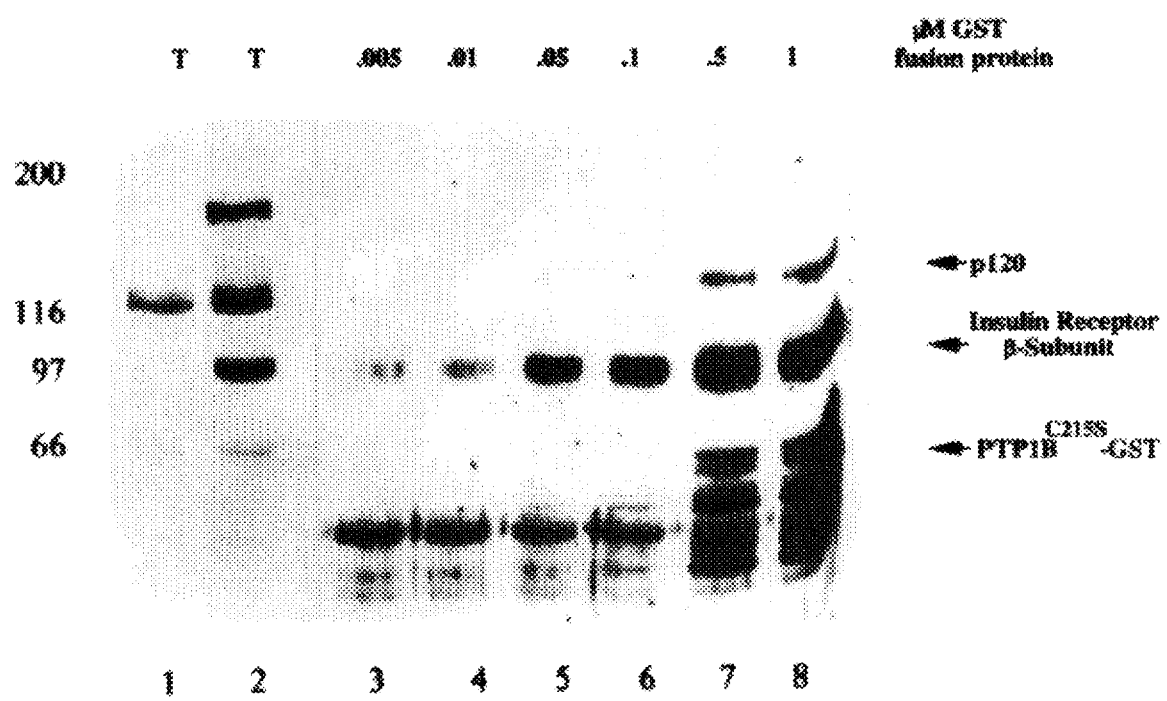
Figure 1C:
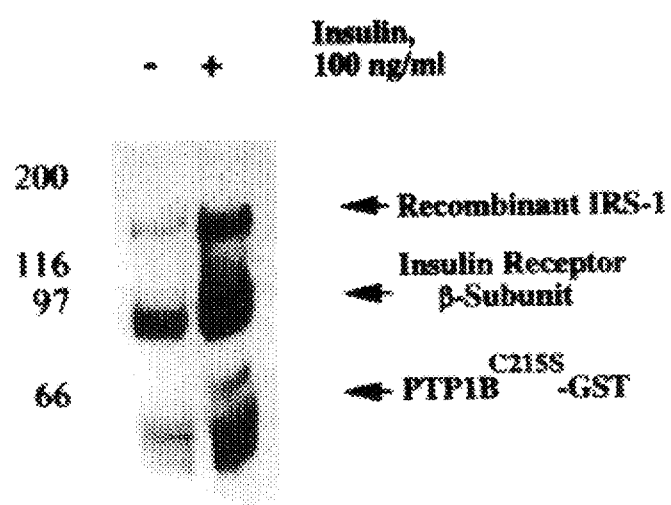

PTP1B is known to dephosphorylate the insulin and IGF-I receptor β-subunits (Milarski, et al., *J. Biol. Chem.* 268:23634–23639, 1993; Staubs, et al., *Biol. Chem.* 269:27186–27192, 1994), but a direct association between the insulin or IGF-I receptor and PTP1B has not been demonstrated. To determine if such an interaction occurs, a GST-fusion protein was used which contained the catalytic domain of rat brain PTP1B, but with a cysteine to serine point mutation rendering the protein catalytically inactive (PTP1B$^{C215S}$-GST) (Guan, et al., *Proc. Natl. Acad. Sci. USA*, 87:1501–1505, 1990; Guan, supra; McClain, et al., *J. Biol. Chem.* 262:14663–14671, 1987). The phosphotyrosine binding site was maintained (Barford, et al., *Science* 263:1397–1404, 1994), thus providing a PTP1B fusion protein which could bind to, but not dephosphorylate, phosphotyrosine substrates. Stimulated insulin receptors were activated, then incubated with increasing concentrations of PTP1B$^{C215S}$-GST. The samples were precipitated with glutathione sepharose, fractioned by gel electrophoresis and immunoblotted with an antiphosphotyrosine antibody. FIG. 1A demonstrates a direct association of the insulin receptor with this fusion protein. FIG. 1B shows a similar experiment using a whole-cell lysates instead of purified receptors. FIGS. 1A–1C show PTP1B$^{C215S}$-GST associates with and is tyrosine-phosphorylated by purified insulin receptors. FIG. 1A shows lectin-purified insulin receptors stimulated with insulin, 100 ng/ml, and activated in the presence of ATP. The samples were incubated for 90 minutes at 4° C. with glutathione sepharose and increasing concentrations of PTP1B$^{C215S}$GST. Precipitates were fractionated by 7.5% SDS-PAGE, transferred to nitrocellulose and immunoblotted with an antiphosphotyrosine antibody. FIG. 1B shows a similar experiment in which cell monolayers of HIRcB were stimulated with 100 ng/ml of insulin, solubilized in lysis buffer and precipitated with increasing concentrations of PTP1B$^{C215S}$-GST. Lanes 1 and 2 represent total whole cell lysates without and with insulin stimulation. FIG. 1C shows partially purified receptors activated in the presence of PTP1B$^{C215S}$-GST and recombinant IRS-1 without (lane 1) and with (lane 2) insulin stimulation (100 ng/ml).

The receptor is again precipitated, as in an 120 kDa phosphoprotein. The identity of the 120 kDa protein is not known. Importantly, IRS-1 (pp 185) is not precipitated by the PTP1B fusion protein. In FIGS. 1A and 1B, there are several protein bands at ~50 kDa which represent the purified PTP1B$^{C215S}$-GST. To further assess insulin-induced tyrosine phosphorylation of the PTP1B fusion in vitro, purified insulin receptors were stimulated with insulin and activated in the presence of PTP1B$^{C215S}$-GST and recombinant IRS-1. The insulin receptor β-subunit, the PTP1B$^{C215S}$ fusion protein, and the recombinant IRS-1 all show a marked increase in tyrosine phosphorylation in response to ligand stimulation (FIG. 1C).

Figure 2:
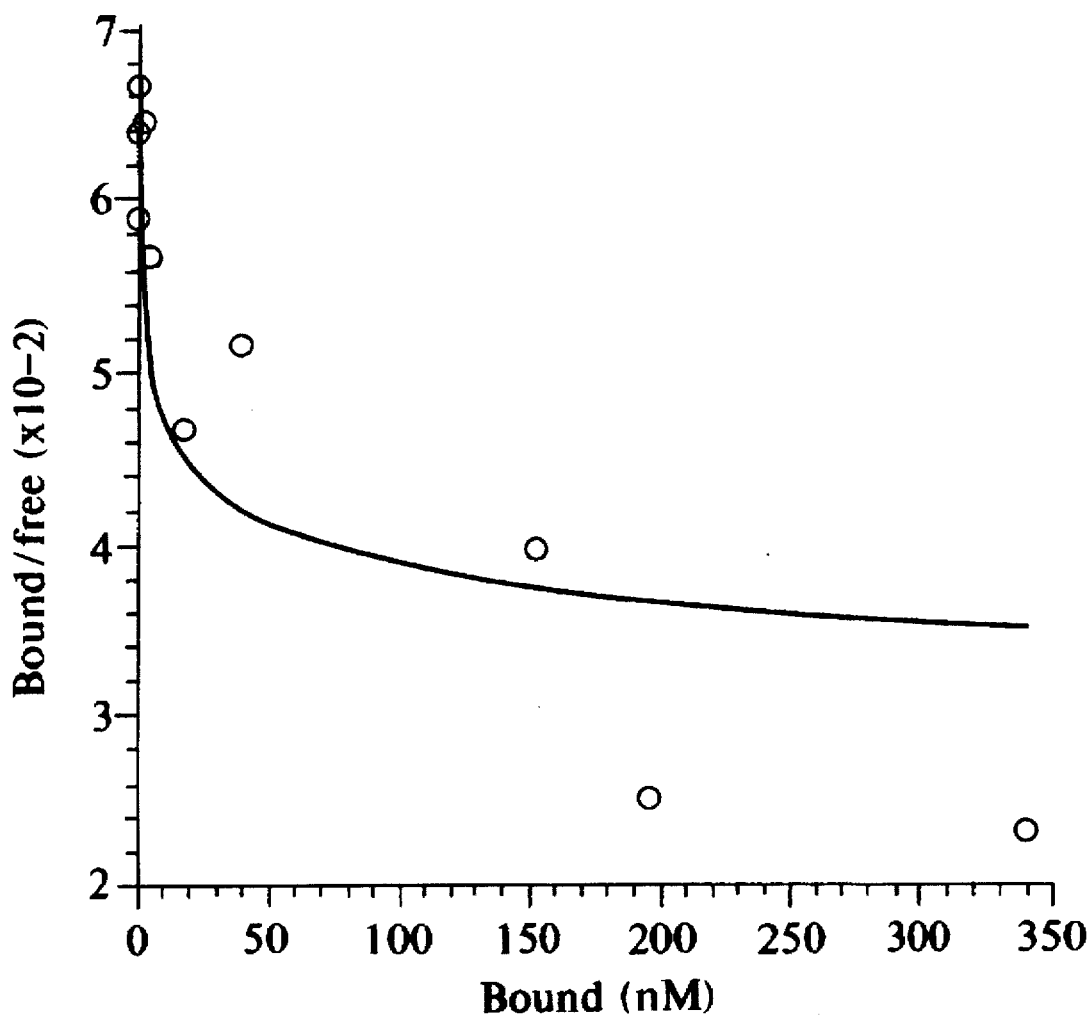
FIG. 2 is a Scatchard analysis of PTP1B$^{2215\ S}$-GST binding to the insulin receptor.

To quantitatively evaluate the binding of the PTP1B$^{C215S}$-GST to the insulin receptor, a binding assay was performed as previously described (Ramachandran, et al., *Biochemistry* 31; 4232–4238, 1992; Zhu, et al., *Proc. Natl. Acad. Sci. USA* 89:9559–9563, 1992; Zuh, et al., *J. Biol. Chem.* 268:1775–1779, 1993) utilizing labeled [S$^{35}$] PTP1B$^{C215S}$-GST obtained by adding Tran$^{35}$S-label to the bacterial culture during induction. FIG. 2 shows a Scatchard analysis of PTP1B$^{C215S}$-GST binding to the insulin receptor. HIRc cells were treated with 100 ng/ml insulin for 10 minutes at 37° C. Insulin receptors were precipitated, and equilibrium binding of the PTP1B$^{C215S}$-GST to the immune complexes was performed. The immunoprecipitated receptors were incubated with 30 nM [S$^{35}$] PTP1B$^{C215S}$ fusion protein in the presence of the indicated concentrations of unlabeled fusion protein. The incubation was carried out at room temperature for 30 minutes, and bound was separated from free by filtration. Quantitation was scintillation counting. The results were transformed to a Scatchard plot.

The activated insulin receptor was immobilized on protein-A agarose beads which were then washed with binding buffer and incubated with the radioactive PTP1B$^{C215S}$-GST in the presence or absence of unlabeled fusion protein under equilibrium binding conditions. After separating the bound from free ligand by filtration, the radiolabeled binding was quantitated in a scintillation counter. The [S$^{35}$] PTP1B$^{C215S}$-GST bound to the activated insulin receptor and was displaced in a concentration-dependant manner. Scatchard analysis revealed a curvilinear plot indicating at least two binding sites. The high affinity binding site has a $K_d$ of approximately 75 nM.

Figure 3:
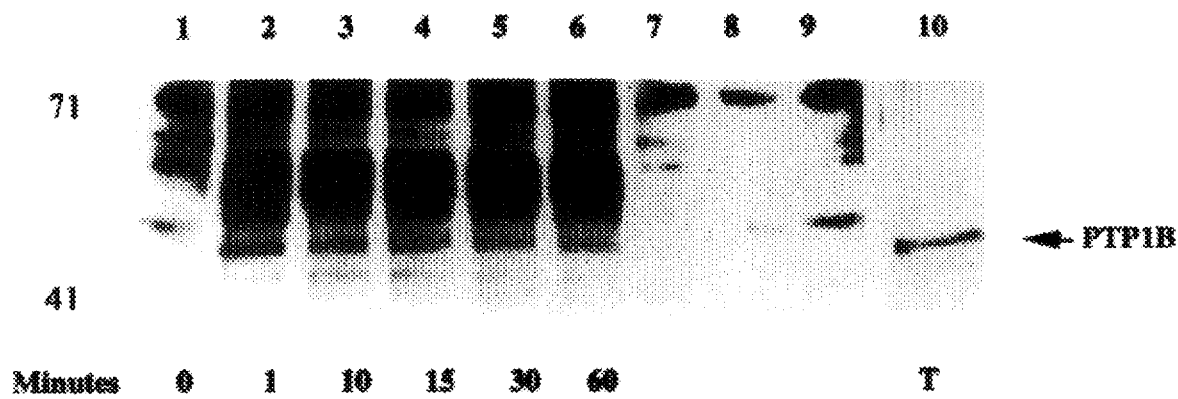
FIG. 3 is an immunoblot showing that PTP1B is precipitated from whole cell lysates by an anti-insulin receptor antibody and is tyrosine-phosphorylated in response to insulin stimulation.

To confirm that PTP1B can associate with the insulin receptor in vivo, monolayers of HIRcB cells were stimulated with insulin at 37° C. for varying time intervals and cells collected into lysis buffer. The cell lysates were then incubated for 4 hours at 4° C. with a monoclonal anti-insulin receptor antibody (1:100). Antibody complexes were collected with Protein A sepharose. The proteins in the precipitate were fractioned by 5–15% non-reducing gel electrophoresis (SDS-PAGE), transferred to nitrocellulose and immunoblotted with an antiphosphotyrosine antibody (FIG. 3, lanes 1–9) or an antiPTP1B antibody (lane 10). Lane 7 represents denatured antibody alone, lane 8 represents non-denatured antibody alone and lane 9 represents an irrelevant mouse anti-trk antibody precipitation of a cell lysate stimulation with insulin for 10 minutes. A protein of 50 kDa is precipitated by the anti-insulin receptor antibody and is tyrosine phosphorylated after one minute of insulin stimulation. This protein runs at the identical molecular mass of PTP1B suggesting that PTP1B can associate with the receptor and undergo tyrosine phosphorylation following insulin stimulation.

Three phosphopeptides modeled after three regions of the insulin receptor known to be important autophosphorylation sites (Riedel, supra; Thies, et al., *J. Biol. Chem.* 265:10132–10137, 1990; Backer, et al., *J. Biol. Chem.* 265:16450–16545, 1990; McClain, *J. Biol. Chem.* 265:21363–21367, 1990; Tavare, et al., *Biochem. J.* 253:783–788, 1988; Ahmad, et al., *J. Biol. Chem.* 270:20503–20508, 1995; Shoelson, et al., *Proc. Natl. Acad. Sci. USA* 89:2027–2031, 1992) were constructed to help localize the PTP1B receptor binding site. These regions included the receptor triple tyrosine kinase domain including tyrosines 1146, 1150 and 1151 (pYpYpY), the NPXY domain including tyrosine 960 (NPXpY), and the C-terminal region including tyrosine 1322 (pY1322). Experiments were performed examining the ability of the PTP1B$^{C215S}$-GST to precipitate the insulin receptor in the presence of increasing concentrations of each of the three phosphopeptides. In these experiments, an RPXpY peptide was used in place of the NPXpY phosphopeptide because HPLC analysis of the NPXpY peptide indicated conformational changes which we believe prevented consistent phosphotyrosine binding.

Figure 4A:
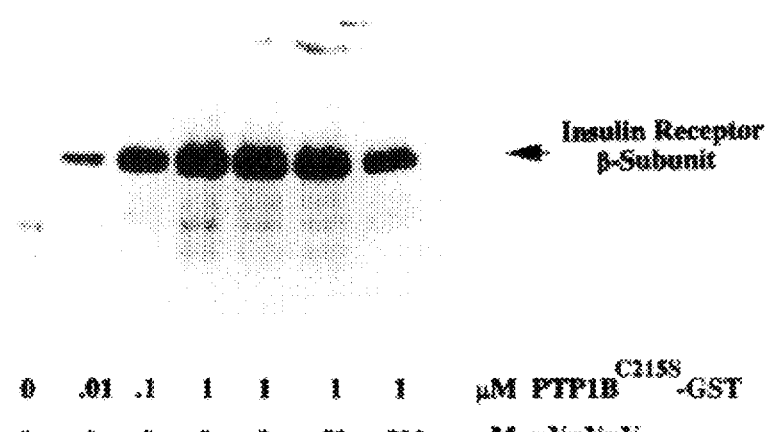
FIGS. 4A–4B show at a set of immunoblots of precipitates (FIG. 4A) and supernatants (FIG. 4B) showing insulin receptor binding to PTP1B$^{C215S}$-GST inhibited by the triple tyrosine phosphopeptide, pYpYpY.
Figure 4B:
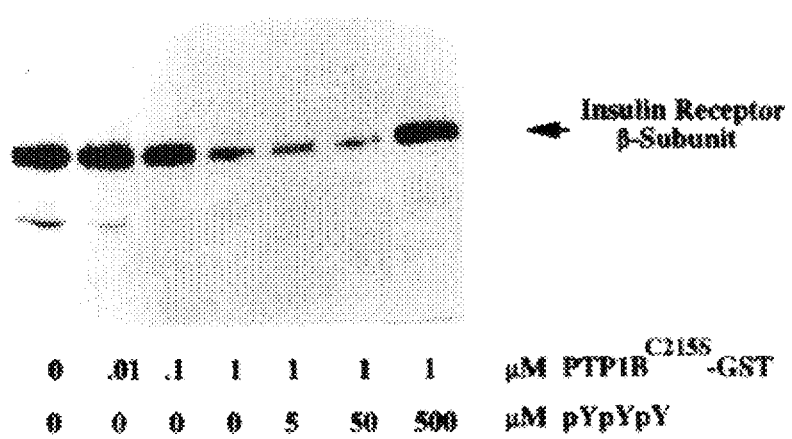

FIGS. 4A–4B show insulin receptor binding to PTP1B$^{C215S}$-GST is inhibited by the triple tyrosine phosphopeptide. Purified insulin receptors were activated in the presence of insulin and ATP and were incubated with increasing concentrations of PTP1B$^{C215S}$-GST, glutathione sepharose, and increasing amounts of the triple tyrosine phosphopeptide, pYpYpY. Precipitates and supernatants were fractionated by 7.5% SDS-PAGE, transferred to nitrocellulose and immunoblotted with an antiphosphotyrosine antibody. FIG. 4A shows that the insulin receptor is precipitated by increasing concentrations of PTP1B$^{C215S}$-GST, but that this precipitation is inhibited by the presence of 500 µM of the triple tyrosine kinase domain phosphopeptide. This is clearly demonstrated in both the precipitates and the supernatants. The kinase domain phosphopeptide can, therefore, bind the PTP1B$^{C215S}$-GST making it unavailable for binding to the insulin receptor β-subunit.

Figure 5A:
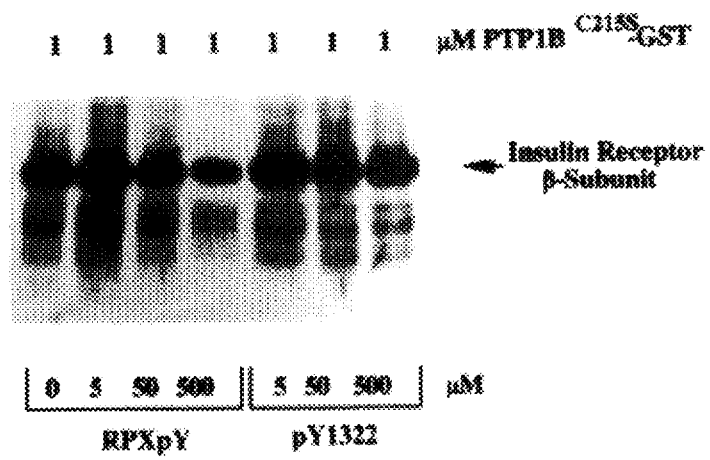
FIGS. 5A–5B show a set of immunoblots of precipitates (FIG. 5A) and supernatants (FIG. 5B) showing insulin receptor binding to PTP1B$^{C215S}$-GST is inhibited by the RPXpY and p1322 phosphopeptides.
Figure 5B:
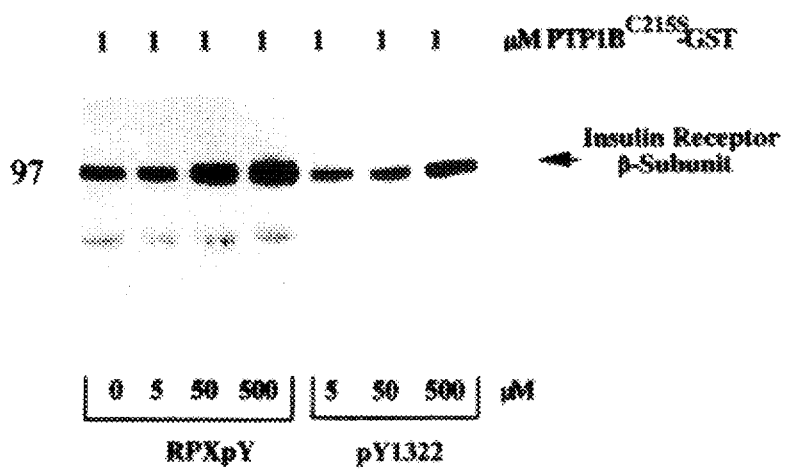

The ability of the NPXY domain and the C-terminal domain peptides to inhibit the insulin receptor interaction with PTP1B was evaluated. FIGS. 5A–5B show insulin receptor binding to PTP1B$^{C215S}$-GST is inhibited by the RPXpY and the pI322 phosphopeptides. Purified insulin receptors were activated in the presence of insulin and ATP and were incubated with increasing concentrations of PTP1B$^{C215S}$-GST, glutathione sepharose, and increasing amounts of the either the RPXpY or the pY1322 phosphopeptide. Precipitates and supernatants were fractionated by 7.5% SDS-PAGE, transferred to nitrocellulose and immunoblotted with an antiphosphotyrosine antibody. FIGS. 5A–5B show that RPXpY and pY1322 can also inhibit insulin receptor precipitation by the inactive PTP1B fusion protein. RPXpY inhibits the insulin receptor: PTP1B fusion protein interaction at a concentration of ~50 μM and pY1322 inhibits receptor precipitation at ~500 μM.

Figure 6A:
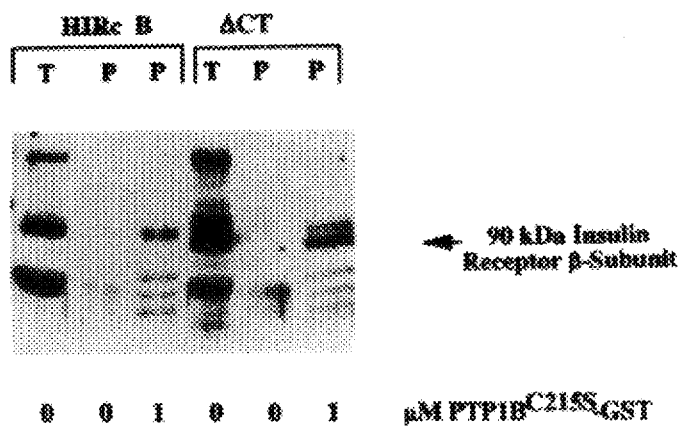
FIGS. 6A–6C show a set of immunoblots of PTP1B$^{C215S}$-GST precipitation of mutant insulin receptors.
Figure 6B:
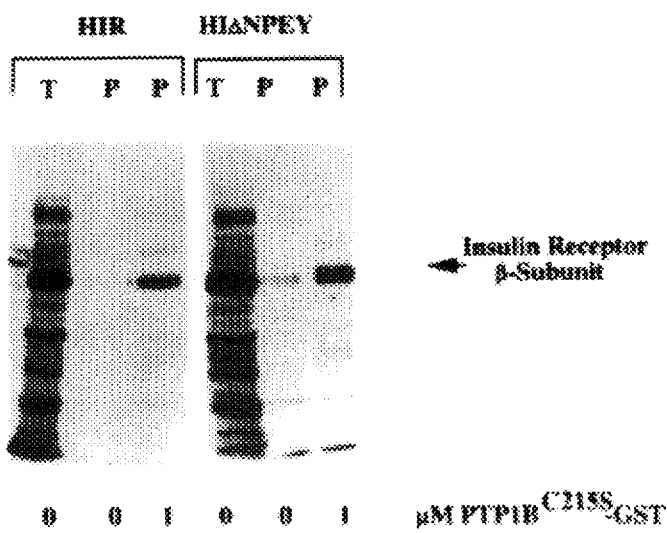
Figure 6C:
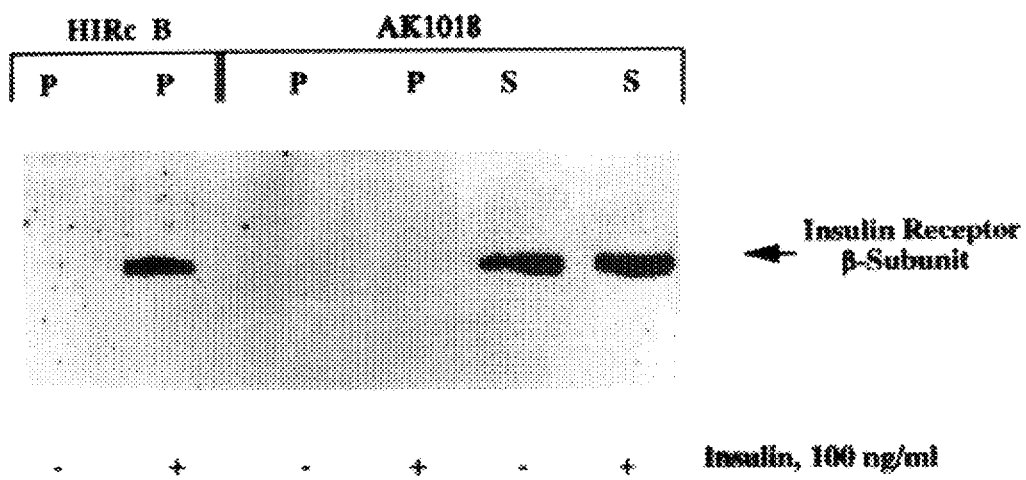

To further explore the interaction between PTP1B and the insulin receptor, the ability of PTP1B$^{C215S}$-GST to precipitate receptors missing various tyrosine residue was determined. ΔCT cells express a mutant insulin receptor truncated at position 1300. This receptor is missing the C-terminal 43 amino acids containing tyrosines 1316 and 1322. FIGS. 6A–6C show PTP1B$^{C215S}$-GST precipitation of mutant insulin receptors. FIG. 6A shows partially purified receptors from HIRc B cells (lanes 1–3) or from ΔCT cells (lanes 4–6) were activated in the presence of insulin and ATP and were incubated with glutathione sepharose and PTP1B$^{C215S}$-GST, 1 μM, where indicated. Lanes 1 and 4 in FIG. 4A and B represent total cell lysates (T). Samples were fractioned by SDS-PAGE, transferred to nitrocellulose and immunoblotted with an antiphosphotyrosine antibody. FIG. 6B shows cell monolayers from HIR (lanes 1–3) or from HIANPEY cells were stimulated with insulin, 100 ng/ml, for one minute at 37° C. and were collected into lysis buffer. Cell lysates were then treated as described above. FIG. 6C shows unstimulated and stimulated partially purified insulin receptors from HIRc B (lanes 1,2) or AK1018 (lanes 3–6) were activated in the presence of ATP and were incubated with glutathione sepharose and PTP1B$^{C215S}$-GST, 1 μM, where indicated. Lanes 1–4 are precipitates and lanes 5 and 6 are supernatants.

As seen in FIG. 6A, lanes 3 and 6, the PTP1B fusion protein precipitates the wild-type and the ΔCT insulin receptors in comparable fashion. A similar experiment is depicted in FIG. 6B, this time showing precipitation of the normal human insulin receptor by PTP1B$^{C215S}$-GST in lane 3. Lane 6 shows that a mutant insulin receptor with a deletion of the NPEY domain, including tyrosine 960, can be precipitated by PTP1B$^{C215S}$-GST. The inactive PTP1B fusion protein again does not precipitate IRS-1 (pp185) from these whole cell lysates.

To determine if tyrosine phosphorylation of the triple tyrosine region of the insulin receptor is necessary for PTP1B$^{C215S}$-GST binding, the AK1018 cell line which over-expresses a kinase-defective insulin receptor with a point mutation in the ATP binding site at position 1018 was examined. The activated wild-type insulin receptor was easily precipitated by the fusion protein, but the insulin-stimulated mutant receptor was not precipitated. These data suggest that activation of the receptor's triple tyrosines in the kinase domain is necessary for the interaction of PTP1B with the insulin receptor.

Figure 7A:
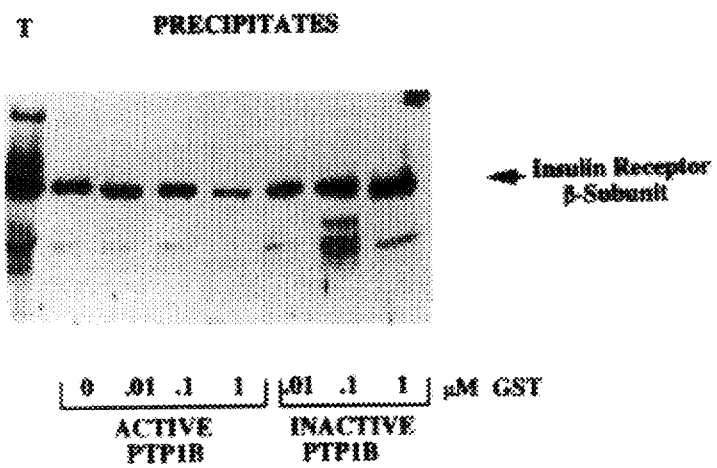
FIGS. 7A–7B show a set of immunoblots of precipitates (FIG. 7A) and supernatants (FIG. 7B) of HIRc B cells stimulated with insulin and activated in the presence of ATP and incubated with PTP1B-GST, PTP1B$^{C215S}$-GST, or p85-GST.
Figure 7B:
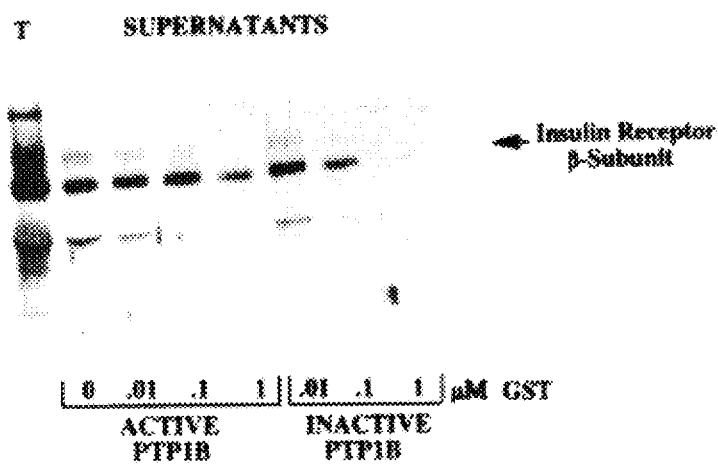

The function of PTP1B appears to be to dephosphorylate the receptor, thus preventing receptor association with secondary signaling substrates such as SH2-domain containing proteins. To test this hypothesis, partially-purified activated insulin receptors were incubated with 1 μM of p85-GST, increasing concentrations of the catalytically-active PTP1B-GST or of the inactive PTP1B-GST, and glutathione sepharose. FIGS. 7A–7B shows catalytically-active PTP1B-GST dephosphorylates the insulin receptor and prevents precipitation by the p85-GST. Partially purified insulin receptors from HIRcB were stimulated with insulin and activated in the presence of ATP. Samples were then incubated for 90 minutes at 4° C. with increasing concentrations of the PTP1B-GST or the PTP1B$^{C215S}$-GST, 1 μM p85-GST, and glutathione sepharose. Precipitates (FIG. 7A) and supernatants (FIG. 7B) were fractionated by SDS-PAGE, transferred to nitrocellulose and immunoblotted with an antiphosphotyrosine antibody. Lane 1 in each FIG. 7A and FIG. 7B represent totals.

The p85 subunit of phosphatidylinositol-3-kinase is an important downstream signaling molecule of the insulin receptor and binds directly to the insulin receptor at tyrosine 1322 (McClain, supra). FIG. 7A, lane 2, shows that p85-GST was able to precipitate the insulin receptor β-subunit in the absence of the active PTP1B-GST, but this interaction was markedly inhibited as increasing concentrations of the PTP1B-GST were added (lanes 3 and 4). Overall receptor tyrosine phosphorylation was decreased, as is evidenced by the decrease in receptor tyrosine phosphorylation in the supernatants, but this generalized dephosphorylation must include tyrosine 1322. This in vitro dephosphorylation does not occur when the PTP1B$^{C215S}$-GST was used. In fact, insulin receptor precipitation was increased in the presence of both fusion proteins (lanes 5–8). These data suggest that PTP1B inhibits insulin receptor signal transduction by dephosphorylating phosphotyrosine residues such as tyrosine 1322, thereby preventing receptor interaction with downstream signaling molecules such as p85.

Although the invention has been described with reference to the presently preferred embodiment, it should be understood that various modifications can be made without departing from the spirit of the invention. Accordingly, the invention is limited only by the following claims.

I claim:

1. A method for determining whether a composition inhibits protein tyrosine phosphatase 1B (PTP1B) binding to phosphorylated insulin receptor rather than phosphatase activity, said method comprising:

incubating the composition with PTP1B polypeptide or with a recombinant cell expressing PTP1B, together with a phosphorylated insulin receptor, for a time and under conditions sufficient to allow the PTP1B and phosphorylated insulin receptor to bind; and determining the composition's inhibition of PTP1B binding to the insulin receptor rather than phosphatase activity.

* * * * *